(12) United States Patent
Naybour et al.

(10) Patent No.: US 12,396,859 B2
(45) Date of Patent: Aug. 26, 2025

(54) TRIAL PATELLA COMPONENT KIT

(71) Applicant: Eventum Orthopaedics Limited, Leeds (GB)

(72) Inventors: John Naybour, Ilkley (GB); Mark Clatworthy, Auckland (NZ)

(73) Assignee: Eventum Orthopaedics Limited, London (GB)

(*) Notice: Subject to any disclaimer, the term of this patent is extended or adjusted under 35 U.S.C. 154(b) by 287 days.

(21) Appl. No.: 17/999,996

(22) PCT Filed: May 20, 2021

(86) PCT No.: PCT/GB2021/051218
§ 371 (c)(1),
(2) Date: Aug. 3, 2023

(87) PCT Pub. No.: WO2021/240135
PCT Pub. Date: Dec. 2, 2021

(65) Prior Publication Data
US 2024/0016618 A1   Jan. 18, 2024

(30) Foreign Application Priority Data

May 27, 2020 (GB) .................................... 2007877
Dec. 7, 2020 (GB) .................................... 2019210

(51) Int. Cl.
*A61F 2/38* (2006.01)
*A61B 17/15* (2006.01)
(Continued)

(52) U.S. Cl.
CPC .......... *A61F 2/3877* (2013.01); *A61B 17/158* (2013.01); *A61F 2/4657* (2013.01);
(Continued)

(58) Field of Classification Search
CPC ............ A61F 2/4657; A61F 2002/3067; A61F 2002/4666; A61F 2/3877; A61F 2/4684; A61F 2002/30616; A61B 17/158
See application file for complete search history.

(56) References Cited

U.S. PATENT DOCUMENTS 5,470,354 A   11/1995 Hershberger et al.
6,855,150 B1   2/2005 Linehan
(Continued)

FOREIGN PATENT DOCUMENTS

WO   2019006370   1/2019
WO   2020037380   2/2020

OTHER PUBLICATIONS

Search Report dated Nov. 11, 2020 for Application No. GB2007877.0 (6-pages).
(Continued)

*Primary Examiner* — Samuel S Hanna
(74) *Attorney, Agent, or Firm* — EIP US LLP

(57) ABSTRACT

A kit for use in knee replacement surgery includes a trial patella component and a patella implant component. The trial patella component includes a backing plate having a backing surface for positioning against a patient's patella, and at least one sensor which can generate a signal corresponding to the compressive load applied to the trial patella component, and a first bearing plate which can be fitted to the backing plate and which, when fitted to the backing plate, provides a bearing surface for articulation against a bearing surface on the patient's femur. The patella implant component has a backing surface for fixation to a patient's patella instead of the backing surface of the trial patella component, and a bearing surface for articulation against a femoral bearing surface. The thickness of the patella implant component is greater than the thickness of the trial patella (Continued)

component when the first bearing plate is fitted to the backing plate, the difference between the said thicknesses being at least about 1 mm.

14 Claims, 14 Drawing Sheets

(51) Int. Cl.
　　*A61F 2/46*　　(2006.01)
　　*A61F 2/30*　　(2006.01)
(52) U.S. Cl.
　　CPC .. *A61F 2/4684* (2013.01); *A61F 2002/30616* (2013.01); *A61F 2002/4666* (2013.01)

(56) References Cited

U.S. PATENT DOCUMENTS

2009/0005708 A1　　1/2009　Johanson et al.
2021/0137704 A1*　5/2021　Angibaud ............. A61F 2/4657

OTHER PUBLICATIONS

International Search Report and Written Opinion for International Application No. PCT/GB2021/051218, dated Jul. 23, 2021, (15 pages).

* cited by examiner

TRIAL PATELLA COMPONENT KIT

BACKGROUND

This invention relates to a trial patella component kit for use in knee replacement surgery.

Procedures used in total knee replacement have been developed with a focus on positioning the femoral and tibial implant components to balance the flexion extension gaps. Two approaches to achieving accurate positioning of the implant components are referred to as the measured resection and balanced approaches.

The measured resection approach focuses on measuring the amount of bone resected from the femur and tibia and replacing this bone with implant components. Compromises have to be made when positioning the components. Firstly, the implant components are three-dimensional devices which are being positioned by the surgeon during surgery based on linear measurements which are made during the course of the procedure and which are prone to errors. These errors in measurement can compound, resulting in inaccurate positioning of the components. Secondly all patients have different sized bones and there are limited sizes of implants. This results in the surgeons having to compromise on the selected size and position of the implant. This can lead to the collateral ligaments surrounding the knee being imbalanced. The surgeon can perform releases of the medial and lateral collateral ligaments to address this imbalance. However this is a difficult procedure because the ligaments impact the balance of the knee in three dimensions. This means that releasing a ligament to balance the ligaments in extension can result in the ligaments being imbalanced when the knee is flexed. These various adjustments which are made during the course of the replacement procedure mean that the positions of the external surfaces of the femoral implant component will frequently not correspond to the positions of the surfaces of the patient's natural femur.

The balanced approach to knee surgery focuses on positioning the implant components in such a way as to balance the ligaments. The medial and lateral collateral ligaments are tensioned in flexion and extension and the implant components are positioned in order to balance the ligaments in flexion and extension. The positions of the external surfaces of the femoral implant component are frequently different from the positions of the surfaces of the patient's natural femur, including for example in the anterior posterior position and the superior inferior position, and in femoral rotation. One of the key elements of the balanced approach has been the adjustment of the femoral resection depth in extension to match the flexion gap. With the balanced surgical approach, the limitation of femoral component sizes is an additional factor impacting the position of the femoral component.

In both surgical approaches the resection of the patella is based on a measurement of the patella thickness before surgery. The aim of the surgery is to resect bone from the patella and replace this thickness of bone with the patella implant, where the thickness of the resected bone is measured with reference to the thickness of the patella implant. In both approaches there is no adjustment to the patella resection, and this can result in a change to the balance of the patella-femoral joint as a result of this procedure which will potentially lead to reduced function of the joint and/or pain long term.

US-A-2003/163137 and US-A-2007/233142 disclose devices which can be used to resect a patella without everting it. The devices have features for gripping the patella and a cutting guide to facilitate guiding a resection saw to cut a desired amount of the dome on the posterior surface of the patella.

US-A-2009/183740 discloses apparatus for use in tracking movement of a patella when a knee is manipulated during a knee replacement surgical procedure. Information concerning the movement of the patella during articulation of the joint enables incorrect positioning of or more of the components of the knee joint to be identified.

Modular trial components have been used in which modularity allows a surgeon to adjust the size of the patella implant based on an assessment of anthropometric fit and joint laxity. This modularity has been designed to help surgeons adjust the thickness of the selected implant by observing the tracking of the patella. For example, US-A-2014/277523 discloses a modular patella trial system which includes an articulation element and a series of sizing elements. Each sizing element has a thickness which is different from that of the other sizing elements.

U.S. Pat. No. 5,470,354 discloses trial patella components for use in combination with trial tibial components to determine forces on a knee joint. At least one of the components is a permanent component and at least one other component is a temporary component.

WO2020/037380 discloses a sensor device for use in joint surgery, the sensor device comprising a trial implant with a sensor disposed over a contact surface thereof, and a spacer device for contacting a resected bone surface and the sensor.

US-A-2009/005708 discloses trial patella components which have different thicknesses and which are used with a load sensor matrix. The disclosed system allows the effect of patella thickness on load distribution to be determined, and allows a surgeon to make a more accurate bone resection.

SUMMARY

This invention provides a kit for use in knee replacement surgery, which comprises a patella implant component for fixation to a patient's patella and for articulation against an implanted femoral component, and a trial patella component. The thickness of the patella implant component is greater than the thickness of the trial patella component.

In one aspect, the invention therefore provides a kit for use in knee replacement surgery, which comprises:
a. a trial patella component comprising:
  i. a backing plate having a backing surface for positioning against a patient's patella, and at least one sensor which can generate a signal corresponding to the compressive load applied to the trial patella component, and
  ii. a first bearing plate which can be fitted to the backing plate and which, when fitted to the backing plate, provides a bearing surface for articulation against a bearing surface on the patient's femur,
b. a patella implant component having a backing surface for fixation to a patient's patella instead of the backing surface of the trial patella component, and a bearing surface for articulation against a femoral bearing surface,
  in which the thickness of the patella implant component is greater than the thickness of the trial patella component when the first bearing plate is fitted to the backing plate, the difference between the said thicknesses being at least about 1 mm.

The kit provided by the invention includes a trial patella component which can be positioned against the prepared surface (usually a planar surface formed by a resection step)

of the patella and used during steps in a knee replacement procedure to plan the procedure and to prepare the component bones of the joint, where the thickness of the trial component is less than the thickness of the ultimate implant component. This allows the patella to be resected again to create a surface which the ultimate implant component is fixed to. The kit therefore provides an opportunity to create a resected surface on the patella for the ultimate implant component which takes account of the planning and preparation steps which are performed with reference to the prepared surface which is used with the trial patella component.

The trial patella component for use in the present invention may be provided separately to the patella implant component. For example, the trial patella component may be provided for use with a specific patella implant obtained separately, or for use with a patella implant separately obtained (or held in stock) by the user.

The trial patella component is used to identify an appropriate location for the plane of the patella resection so that the patella is appropriately located relative to the other bones of the knee. These results are available notwithstanding the fact that the shape and configuration of the trial component is different from the shape and configuration of the implant component. The trial component is also used to provide the surgeon with information concerning the structure of a patient's native joint.

The kit provided by the invention can be used in knee replacement surgery to assess tension in soft tissue which is connected to a patient's patella, in particular in the quadriceps. The tension of the quadriceps throughout the range of motion of the joint is affected by the thickness of the patella: the tension is greater when the thickness of the patella is greater. The invention provides the possibility of obtaining information about tension in the soft tissue in the patient's native knee when it is articulated, and then planning the preparation of the patella for receiving the patella component of the knee joint prosthesis so that the soft tissue tension after surgery is approximately the same as the tension before surgery, or differs from the tension pre-surgery in a way that is selected by the surgeon.

The invention also provides a method of knee replacement surgery which comprises:
a. performing a first resection on the patient's patella,
b. fitting to the resected patella a trial patella component comprising:
   i. a backing plate having at least one sensor which can generate a signal corresponding to the compressive load applied to the backing plate, and
   ii. a first bearing plate which can be fitted to the backing plate and which, when fitted to the backing plate, provides a bearing surface for articulation with a bearing surface on the patient's femur,
c. articulating the knee joint to obtain information from the sensor concerning tension in soft tissue which is connected to the patella as the patella articulates against the patient's existing femoral bearing surface,
d. fitting a femoral trial component to the patient's femur,
e. articulating the knee joint to obtain information from the sensor concerning tension in soft tissue which is connected to the patella as the patella articulates against the surface provided by the femoral trial component,
f. identifying the location of a second resection of the patella to receive a patella implant component whose thickness is greater than that of the trial patella component, to provide a desired tension in soft tissue which is connected to the patella as the patella articulates against the femoral implant component in the completed replacement joint,
g. performing the second resection on the patient's patella, and
h. fitting the patella implant component to the patient's patella.

The invention makes possible the selection of an appropriate soft tissue tension after surgery because the thickness of the trial patella component is less than that of the patella implant component. This means that the amount of tissue that is removed from the patella in a first resection to allow the trial patella component to be fitted to the patella is less than the total amount of tissue that will be removed from the patella as a result of the second resection which then allows the patella implant component to be fitted. The patella fitting will accommodate changes in femoral component position as a result of the balanced approach or measured resection approach to fitting the femoral component position.

When a reference is made in this document to the thickness of a component such as a patella implant component or a trial patella component, the thickness is measured at the point on the bearing surface of the component at which the thickness is a minimum. The bearing surface of the component is the surface which contacts a femoral bearing surface such as the bearing surface on the patient's native femur, a femoral bearing surface on a trial femoral component, or a femoral bearing surface on a femoral component of a knee joint prosthesis during normal articulation of the prosthesis. Frequently, this will be towards an edge of the patella bearing surface, although the component (patella implant component or trial patella component) might extend beyond the point on the bearing surface at which the thickness is a minimum, for example as a result of tapering of the edge of the component. The thickness of the component might have more than one minimum, especially at or towards medial and lateral edges of the component.

Optionally, the difference between the thickness of the patella implant component and the thickness of the trial patella component which is provided by the backing plate and the first bearing plate is at least about 3 mm or at least about 5 mm. A larger difference between the thicknesses can allow for a larger range of adjustment in the final depth of the patella after fitting of the implant component.

Optionally, the thickness of the trial patella component which is provided by the backing plate and the first bearing plate is not more than about 6 mm. It can be preferred that the thickness of the trial patella component which is provided by the backing plate and the first bearing plate is not more than about 5 mm, for example about 4 mm.

Optionally, the kit includes a differential thickness bearing plate which can be fitted to the backing plate instead of the first bearing plate and which, when fitted to the backing plate, provides a bearing surface for articulation with a bearing surface on the patient's femur, in which the thickness of the differential thickness bearing plate is less than the thickness of the first bearing plate. The inclination of the trial patella component, measured between the backing surface provided by the backing plate and the bearing surface provided by the first and differential thickness bearing plates, is the same irrespective of the bearing plate that is selected.

The kit can include one or more differential thickness bearing plates (for example two or three differential thickness bearing plates) whose thicknesses are different from one another and greater than that of the first bearing plate. The kit can include one or more differential thickness bearing plates whose thicknesses are different from one another and less than that of the first bearing plate. It can be preferred that the kit includes at least one differential thickness bearing plate whose thickness is less than that of the first bearing plate and at least one differential thickness bearing plate whose thickness is greater than that of the first bearing plate.

Optionally, the kit includes a differential inclination bearing plate which can be fitted to the backing plate instead of the first bearing plate and which, when fitted to the backing plate, provides a bearing surface for articulation against a bearing surface on the patient's femur, in which the difference in thickness between the first and second opposite edges of the first bearing plate is different from the difference in thickness between the corresponding first and second edges of the differential thickness bearing plate. The inclination of the trial patella component, measured between the backing surface provided by the backing plate and the bearing surface provided by the first and differential inclination bearing plates, varies according to which of the bearing plates is selected. The kit can include one or more differential inclination bearing plates (for example two or three differential inclination bearing plates) in which the difference in thickness differences defined above in this paragraph relative to the first bearing plate is different from one differential inclination bearing plate to another.

The first and second opposite edges might be medial and lateral edges respectively when the bearing plate is fitted to the backing plate. The first and second opposite edges might be superior and inferior edges respectively when the bearing plate is fitted to the backing plate.

The axis of inclination of the differential inclination bearing plate need not be perpendicular to an edge of the bearing plate. Accordingly, it is an option that the kit includes a differential inclination bearing plate which can be fitted to the backing plate instead of the first bearing plate and which, when fitted to the backing plate, provides a bearing surface for articulation against a bearing surface on the patient's femur, in which the difference in thickness between the first and second opposite corners of the first bearing plate is different from the difference in thickness between the corresponding first and second corners of the differential thickness bearing plate.

The kit can include the first bearing plate together with at least one of one or more (for example two or three) differential thickness bearing plates and one or more (for example two or three) differential inclination bearing plates.

The kit can include at least three bearing plates or at least four bearing plates or at least five bearing plates.

When the kit includes more than one differential thickness bearing plate, it can be preferred that the difference in thickness between a pair of differential thickness bearing plates whose thickness is closest is at least about 0.5 mm. When the kit includes more than one differential thickness bearing plate, it can be preferred that the difference in thickness between a pair of differential thickness bearing plates whose thickness is closest is not more than about 2 mm, or not more than about 1.5 mm. It can be preferred that the difference in thickness between a pair of differential thickness bearing plates whose thickness is closest is from about 0.7 mm to about 1.3 mm, especially about 1 mm.

Optionally, the kit includes a first shim which can be fitted between the backing plate and the first bearing plate or between the backing plate and a differential thickness or differential inclination bearing plate. The kit can include a second shim which can be fitted between the backing plate and the first bearing plate or between the backing plate and a differential thickness or differential inclination bearing plate instead of or in addition to the first shim. Optionally, the thickness of the second shim is different from the thickness of the first shim. Optionally, the difference in thickness between the medial and lateral edges of the first shim is different from the difference in thickness between the medial and lateral edges of the second shim.

A combination of a bearing plate and one or more shims can be used to vary the thickness of the trial patella component, and optionally to vary the inclination of the trial patella component measured between the backing surface provided by the backing plate and the bearing surface provided by the bearing plate.

The possibility that is provided by the invention of varying the thickness of the trial patella component, and optionally of varying the inclination of the trial patella component provision, allows information to be obtained concerning the tension in the soft tissue which is connected to a patient's patella as the patella articulates against the patient's existing femoral bearing surface (which could be the bearing surface provided by the patient's native femur, or the bearing surface provided by an existing implanted femoral prosthesis component) using the trial patella component (which has been fitted to the patella after an initial resection of the patella to remove a thickness of bone which corresponds approximately to the thickness of the trial patella component). This can be compared with information that is obtained subsequently, after fitting a femoral trial component to the femur, when the patella articulates against the surface provided by the femoral trial component. The tension in the soft tissue can then be increased by changing to a thicker bearing plate in the trial patella component. The tension in the soft tissue can be reduced by changing to a thinner bearing plate in the trial patella component. The balance in the tension in soft tissue on different sides of the joint (for example between medial and lateral sides) can be varied by changing the inclination of the trial patella component.

A surgeon can calculate the correct amount to resect from the patella in order to obtain a desired tension in the quadriceps muscle, for example to match the tension in the muscle prior to the operation, by changing the thickness and optionally also the inclination of the trial patella component by a known amount. The sensors can provide load signals to a data processing device which can store the load data. Information concerning the sensed load can be displayed on a display device such as a monitor. The effect of changing the thickness and/or the inclination of the trial patella component throughout the range of motion of the joint can be observed. This information can help the surgeon to assess the relative suitabilities of different surgical options. For example, it can help the surgeon to match the load applied to the trial patella component by selecting a bearing plate having an appropriate thickness and/or inclination. The amount of additional bone that should be resected from the patella, in order to accommodate the patella implant component can be calculated once the bearing plate with an appropriate thickness and/or inclination has been identified.

The invention therefore allows a surgeon to reconstruct a patient's natural quadriceps balance during knee replacement surgery. The information that is used to select the quadriceps balance in the completed knee can be taken from pre-operative data. However, it is an advantage of the invention that the data used to select the quadriceps balance can be taken from the patient during surgery.

Optionally, the thickness of the patella implant component is at least about 6 mm, for example at least about 7 mm. The thickness of the patella implant component might be up to about 9 mm.

The trial patella component for use in the present invention can be designed for use with a specific patella implant component which is supplied with the trial patella component. Alternatively, the trial patella component could also be used with a patella implant component which is known for use in other surgical procedures and which meets the limitations of the patella implant component which are specified in the claims, especially when guidance is provided to the user of the patella implant component concerning such potential and actual uses. Thus, as noted herein, the trial patella component may be supplied separately from a patella implant component.

In an alternative aspect therefore, the present invention provides a trial patella component for use in knee replacement surgery which comprises:

i. a backing plate having a backing surface for positioning against a patient's patella, and at least one sensor which can generate a signal corresponding to the compressive load applied to the trial patella component, and ii. a first bearing plate which can be fitted to the backing plate and which, when fitted to the backing plate, provides a bearing surface for articulation against a bearing surface on the patient's femur.

In the alternative aspect, the thickness of the trial patella component when the first bearing plate is fitted to the backing plate is preferably less than the thickness of the patella implant with which it is intended to be used, more preferably the difference in said thickness being at least about 1 mm. In particularly preferred embodiments of the alternative aspect, the thickness of the trial patella component when the first bearing plate is fitted to the backing plate is not more than about 6 mm.

It can be preferred that the trial patella component has a handle which extends outwardly from a patient's joint when the trial patella component is positioned with the bearing surface of the first bearing plate in contact with a bearing surface on the patient's femur. A handle can be used to manipulate the trial patella component, for example to position it with a patient's joint, and to remove it from the joint for example to replace a bearing plate with another bearing plate having a different thickness. The handle can be connected to the backing plate; for example the handle and the backing plate can be formed from or as a single piece, such as by cutting them as a single piece from a piece of sheet material. The handle can extend in the transverse plane from the joint. The handle can include a portion which extends inferiorly or superiorly.

It will frequently be preferred that the backing plate will be as thin as possible, consistent with the backing plate being able to provide its required functions such as carrying the sensor components, being resistant to deformation when, with the bearing plate, it articulates against the femoral bearing surface, and having the features which enable it to be fastened to the bearing plate. For example, the thickness of the backing plate (not including features for fastening it to the bearing plate) might be not more than about 2 mm.

The at least one sensor which can generate a signal corresponding to the compressive load applied to the trial patella component may be integral with the backing plate of the trial patella component or may be provided as a separate component for integration with the backing plate in use. For example, the one or more sensors may be in the form of a sensor sheet (a thin sheet having one or more sensors present thereon).

Any suitable sensors can be used as the sensor of the backing plate of the trial patella component of the invention. For example, the sensor on the backing plate can comprise a flexible panel which is acted on by a protrusion on the bearing plate so that, when the trial patella component is placed under a compressive load, the protrusion causes the panel to flex. Preferably, the panel should flex resiliently so that it returns to its unflexed position when a compressive load is removed. The panel can be connected with a strain gauge which can be used to measure the compressive load. It will often be preferred for the backing plate to have at least two flexible panels, especially at least three flexible panels, which are is acted on by respective protrusions on the bearing plate so that, when the trial patella component is placed under a compressive load, the protrusions cause one or more of the panels to flex, so that the backing plate has at least two sensors or at least three sensors. When there is more than one flexible panel, each such panel can have a strain gauge associated with it to measure the compressive load applied to the trial patella component. The trial patella component might incorporate a Wheatstone bridge strain gauge array.

Additionally or alternatively, the backing plate might make use of force sensing resistors to measure a compressive load applied to the trial patella component. For example, one or more force sensing resistors might be mounted on the backing plate to measure a compressive load applied to the trial patella component (either integrally or as a separate sensor sheet). Suitable sensors can include piezoresistive force sensors. It is preferred that the sensors are thin and flexible so that they can be incorporated into the trial patella component. Sensors should be selected so that the range of forces that they can sense includes forces which might be sensed in the trial patella component. Preferably the output from the sensor varies linearly with the applied force, at least over the range of forces which might be sensed when the sensor is in use. An example of a force sensor which might be suitable for many applications is the Flexi-Force HT201 sensor, available from Tekscan Inc.

The backing plate can have at least two sensors which are spaced apart along the superior-inferior axis of the trial patella component.

The backing plate can have at least two sensors which are spaced apart along the medial-lateral axis of the trial patella component.

For example, the backing plate can have three sensors which are spaced apart at the apices of a triangle, for example an isosceles triangle or an equilateral triangle. Two of the sensors can be spaced apart along the medial-lateral axis of the trial patella component, with the third sensor located superiorly relative to the other sensors, especially equidistant from the other sensors.

Optionally, the kit includes a patella implant trial component for temporary fixation to a patient's patella and for articulation against a femoral bearing surface, the thickness of the patella implant trial component corresponding generally to the thickness of the patella implant component. The thickness of the patella implant trial component is greater than the thickness of the trial patella component, at least when the trial patella component comprises the backing plate and the first bearing plate. The patella implant trial component can be used when the joint is articulated using femoral and patella implant trial components to verify that characteristics of the patellofemoral articulation are as intended based on the surgical plan.

Optionally, the kit can include a cutting guide having a support surface which can be engaged by a cutting instrument, and a mount which is configured to locate the cutting guide on a resected surface of the patella so that the cutting instrument is located relative to the resected surface of the patella when it engages the support surface to perform a secondary resection. The mount will preferably be configured so that it fits in a stable fashion on a resected surface of the patella so that the cutting guide can locate a cutting instrument accurately relative to the patella surface. The resected surface of the patella on which the mount for the cutting guide is located will frequently be planar. The mount will then preferably have a corresponding planar surface.

The cutting instrument can be a reamer with a rotating cutting head which can be directed towards the patella to remove tissue and so create a new resected surface. The cutting guide can include at least one tubular insert, in which the reamer cutting head can extend through the insert. The insert can define the depth to which the cutting head is able to cut the patella and the angular orientation of the axis of rotation of the cutting head relative to the patella. The depth or the angular orientation or both can be varied by changing the tubular insert.

The cutting instrument might be a saw with a blade. The cutting guide can provide a support surface for the blade. The support surface can be provided by an internal surface of a slot, or can be exposed.

Optionally, the cutting guide includes a clamp for fastening the cutting guide to the patella with the mount located on a resected surface of the patella. The clamp can include a support plate and a clamp plate, in which the clamp plate and the support plate are capable of movement relative to one another to clamp a patella between them. The cutting guide can then facilitate a stable clamping arrangement where the planar resection surface engages the clamp plate.

A cutting assembly for resecting a patient's patella during knee surgery having features as discussed above is disclosed in UK patent application no. 2017775.4, title A Cutting Assembly for Resecting a Patella, filed by Eventum Orthopaedics Limited on 11 Nov. 2020. Subject matter disclosed in that document is disclosed in this application by this reference to the document.

Optionally, the backing plate has at least one pin which can penetrate a prepared surface of a patient's patella to locate the backing plate on the patella. For example, the backing plate can have two spaced apart pins. A pin can have a sharp tip at its free end to facilitate penetration of the surface of the patella.

Optionally, the backing plate and the first bearing plate of the trial patella component of the present invention may comprise co-operating means to removably fix the backing plate on the bearing plate during use. In preferred embodiments, any additional bearing plates and/or shims included in the kit may also comprise complimentary fixing means. The fixing means hold the bearing plates(s) and shims in a fixed position on the backing plate during use providing use of use and consistency of measurements, and also allow convenient removal of the plates and/or shims to allow alternative plates and shims to be added to the backing plate for multiple measurements to be made.

Any suitable fixing means may be used to removably fix the backing plate on the bearing plate during use in the kits of the present invention. In a first example of suitable means, the bearing plate and the backing plate can be held together by means of cooperating spigot and socket features. For example, the surface of the first bearing plate which contacts the backing plate, and the surface of the backing plate which is contacted by the first bearing plate, can have mating spigot and socket features for locating the first bearing plate on the backing plate. Optionally, the spigot can be provided on the backing plate.

Optionally, the spigot is wider towards its free end than at its opposite root end. The width of the socket at its opening can be smaller than its width towards its other end. Optionally, external surface of the spigot at its widest point is provided by a resiliently deformable material, for example by a sleeve of a resiliently deformable material. This can allow the bearing plate and the backing plate to be pressed together when the deformable material on the spigot is compressed to so that it can be fitted into the socket. The deformable material expands within the socket towards its pre-compressed shape to hold the bearing plate and the backing plate together. An example of a suitable deformable material is a silicone rubber. These features can help to ensure that the backing plate and the bearing plate remain in close surface to surface contact when the trial patella component is in place on a patient's patella during articulation of the patient's joint.

Any additional bearing plates (such as differential thickness or differential inclination bearing plates) included in the kit of the invention may optionally also comprise a socket sized to cooperate with the spigot of the backing plate or vice versa.

In a second example of suitable fixing means, the backing plate may comprise one or more locating pins extending vertically from the surface of the backing plate that faces away from the patella in use, and the first bearing plate (and optionally any other bearing plates and/or shims) may comprise corresponding bores for sliding over the one or more locating pins to locate the bearing plate or shim on the backing plate. Preferably two locating pins and corresponding bores are provided.

The material for the backing plate will be selected according to its intended function, in particular if it includes deformable parts which are intended to flex for the purpose of sensing the compressive load applied to the trial patella component. Suitable materials include any structurally stable material suitable for surgical use, including composite materials, metals and alloys, such as stainless steel or titanium-aluminium-vanadium alloys such as Ti6Al4V alloys.

The material for the bearing plate might be selected from materials commonly used for trial components which are used in orthopaedic joint replacement procedures. Examples include metals such as certain stainless steels, and heat resistant polymers such as polyolefins, polyamides, polyesters and polycarbonates, optionally reinforced with structural fibres; a particular example includes nylon reinforced with glass fibres.

The patella implant components of the present invention will generally be made from materials commonly used for such components. Examples include metals, such as cobalt-chromium alloys and titanium, or plastics, such as polyethylene.

The optional shims used in the present invention may be formed from any suitable material, such as heat resistant polymers, optionally reinforced with structural fibres, or metals such as stainless steel.

The components of the kits of the present invention may be made in any convenient manner, including by 3D printing.

INTRODUCTION TO THE DRAWINGS

The invention is described below by way of example with reference to the accompanying drawings, in which.

FIGS. 22(a) to (c) are views of a patella showing schematically different patella resection steps.

FIGS. 23(a) to (c) are schematic end views of a femur-patella combination which show how the position of the patella resection can be optimised by this invention.

DETAILED DESCRIPTION

Figure 1:
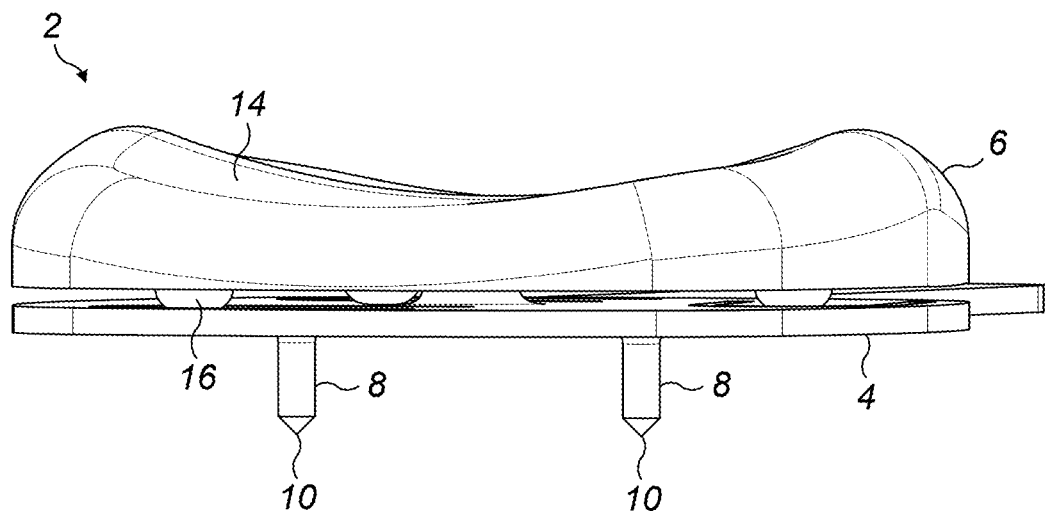
FIG. 1 is a side elevation view of a trial patella component as can be incorporated in the kit of the invention.

Referring to the drawings, FIG. 1 shows a trial patella component 2 which comprises a backing plate 4 and a bearing plate 6. The backing plate 4 has two pins 8 which have pointed tips 10. The bearing plate 6 is located on the backing plate by means of spigot 12 (see FIG. 4) which is received in a socket. A spigot can be provided on the surface of the backing plate which is opposite to the surface on which the pins are provided, and a socket to receive the spigot can be provided on the bearing plate.

The bearing plate 6 has a bearing surface 14 which is contoured for articulation with a bearing surface on a patient's femur. The bearing surface on the femur can be the surface of the patient's natural femur. The bearing surface on the femur can be the surface of a primary femoral implant component which is to be replaced in a revision procedure (in which an already implanted knee joint prosthesis is replaced by a revision prosthesis, for example because of wear or loosening of one or more components of the already implanted prosthesis). The bearing surface on the femur can be the surface of a trial femoral component which is to be replaced by a femoral implant component.

The bearing plate 6 has three protrusions 16 on the surface which is opposite to the bearing surface 14, which are aligned with respective flex panels on the backing plate.

Figure 2:
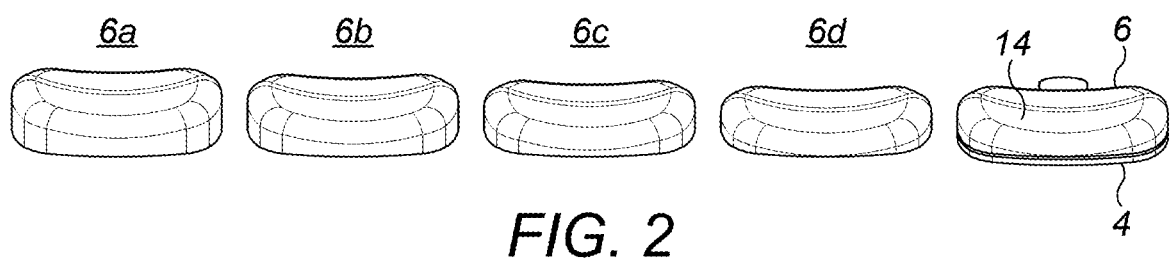
FIG. 2 is an isometric view of a kit which includes a backing plate together with a plurality of bearing plates, with one of the bearing plates mounted on the backing plate to create a trial patella component as shown in FIG. 1.

FIG. 2 shows components of a kit for use in knee replacement surgery which includes the trial patella component 2 shown in FIG. 1. The kit includes four bearing plates 6a, 6b, 6c, 6d in addition to the bearing plate 6 which is shown as part of the trial patella component shown in FIG. 1. The bearing plates differ from one another in terms of their thicknesses. The difference between the thicknesses of any two bearing plates whose thicknesses is closest is 1 mm. Each of the bearing plates has a bearing surface 14, and three protrusions (not shown in FIG. 2) on the surface which is opposite to the bearing surface.

Figure 3:
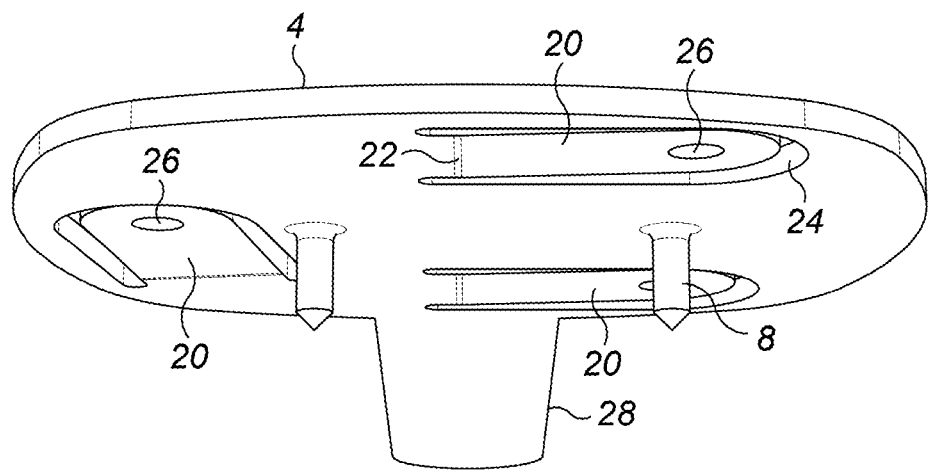
FIG. 3 is an isometric view from below of a backing plate.

FIG. 3 shows the backing plate 4 which has three flexible panels 20. Each of the flexible panels is connected to the main body of the backing plate along one edge 22. A slot 24 separates each panel from the main body of the backing plate along its other edges. A small hole 26 (which is shown as a through hole in the drawing but could be a blind hole which is open only on the surface of the backing plate which faces the bearing plate) is provided in each of the flexible panels. A handle 28 is formed from the same sheet of material as the backing plate, extending from the main body of the backing plate. The thickness of the backing plate is about 1 mm. The width of each of the flexible panels is about 6 mm. The length of each of the flexible panels is about 10 mm. Strain gauges are provided on the backing plate. A strain gauge is associated with each of the flexible panels to measure the strain in each panel as a result of load applied to the backing plate by the bearing plate. The incorporation of a strain gauge in association with a flexible panel of the type shown in FIG. 3 so that readable signals are generated reflecting the strain and therefore the applied load is known.

Figure 4:
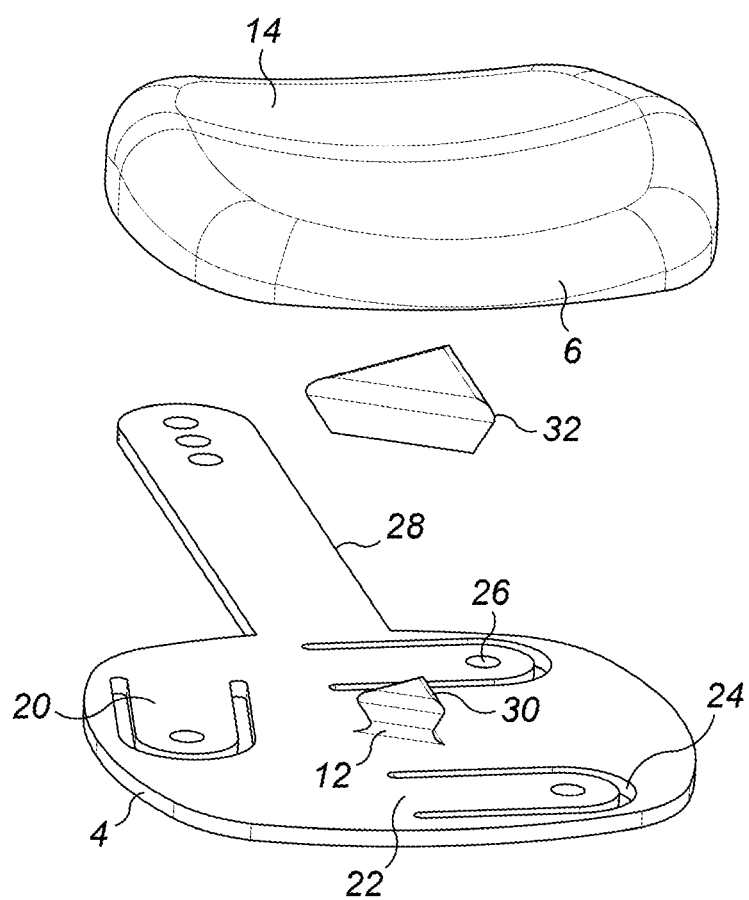
FIG. 4 is an exploded isometric view of a trial patella component as shown in FIG. 1.

FIG. 4 is an exploded isometric view from above of the trial patella component 2, showing in particular the spigot 12 on the backing plate. It is wider at its free end 30 than at its base. A sleeve 32 of a resiliently deformable material fits over the spigot.

Figure 5:
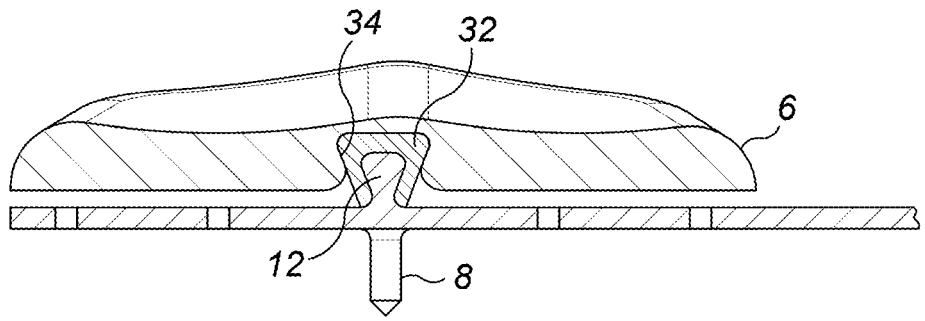
FIG. 5 is a cross-section view of a trial patella component.

FIG. 5 is a cross-section view through the trial patella component shown in FIG. 4, showing the spigot 12 with the sleeve 32 fitted over it, received in a socket 34 in the bearing plate 6. The size of the socket at its open end is slightly smaller than the size of the spigot at its free end when the sleeve is fitted over the spigot, so that the sleeve has to be compressed slightly in order for the spigot to be received in the socket. The use of a resiliently deformable material for the sleeve means that it is able to expand towards the shape and configuration that it had before being compressed, so that separation of the backing plate and the bearing plate is resisted.

Figure 6:
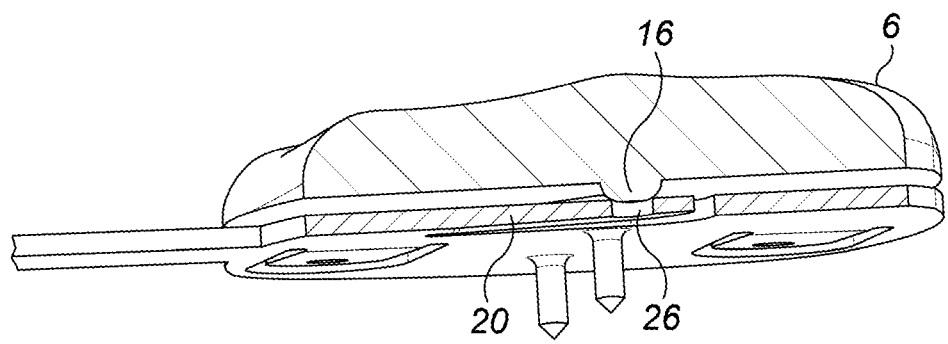
FIG. 6 is an isometric sectional view from one side of a trial patella component.

FIG. 6 is a side elevation of the trial patella component shown in FIG. 4, showing how one of the protrusions 16 on the bearing component engages one of the small holes 26 that is provided in the flexible panels 20 in the backing plate.

The kit includes a patella implant component, and optionally also a patella implant trial component. The designs of these components will closely follow those of existing components. The kit of the invention provides the trial patella component which enables appropriate preparation of a patient's patella to allow use of patella components of existing designs.

The invention has been assessed using bearing plate components of a trial patella component. The bearing plate shown in at least FIGS. 1 to 6 is and has been made by 3D printing. The properties of the material are as follows:

| PROPERTY | TEST METHOD | VALUE |
| --- | --- | --- |
| Colour | — | White |
| Sintered density | ASTM D792 | 0.93 g · cm$^{-3}$ |
| Water absorption, 20° C., 50% Relative Humidity | DIN EN ISO 62 | 0.5 ± 0.2% |
| Water absorption, 24 h in boiling water | | 2.0 ± 0.3% |
| E-Module (x-y plane) | DIN EN ISO 527, | 2000 ± 200 MPa |
| E-Module (z plane) | test speed | 1900 ± 200 MPa |
| Tensile strength (x-y) | 10 mm · min$^{-1}$ | 50 ± 4 MPa |
| Tensile strength (z) | | 42 ± 5 MPa |
| Elongation at break (x-y) | | 11% ± 4% |
| Elongation at break (z) | | 4% ± 2% |
| Vicat softening point | ISO 306 (50° C. · h$^{-1}$ 50N) | 163° C. |

The invention has been assessed using various backing plate components. The backing plate shown in FIGS. 1 to 6 is made from a Ti6Al4V alloy and is subjected to a heat treatment to optimise its physical properties. The properties of the material are as follows:

| Tensile Strength MPa | Yield Strength 0.2% MPa | Elongation % | Hardness |
| --- | --- | --- | --- |
| >930 MPa | >860 MPa | 10% | 33 +/− 2 HBW |

The embodiments shown in FIGS. 1 to 6 include a sleeve of a resiliently deformable material fitted over the spigot on the backing plate component, where the sleeve has been made from a silicone rubber by screen printing. The rubber has a Shore A hardness of 65 (measured according to ASTM D-2240), with a tensile tear strength of between 10 and 12 kgf·cm$^{-1}$ (measured according to ASTM D-624), an elongation to break of between 120 and 170% (measured according to ASTM D-412) and a tensile strength of between 4.0 and 4.5 MPa (measured according to ASTM D-412).

It is estimated that the maximum load to which a patella is subjected throughout the range of motion of a knee in a typical patient is about 200 N. The backing plate is able to measure loads in excess of this, with deformation of the flexible panels in the backing plate in response to the compressive loads applied to the trial patella component through the bearing plate.

Suitable strain gauges for use in the backing plate are capable of measuring strain of up to 10% when a load of up to 200 N is applied to the flexible panels. Signals from the strain gauges can be processed using an appropriate analog to digital converter and an appropriate data processor. An analog to digital converter and a data processor from Friends-of-Fritzing eV have been used in testing.

Figure 7:
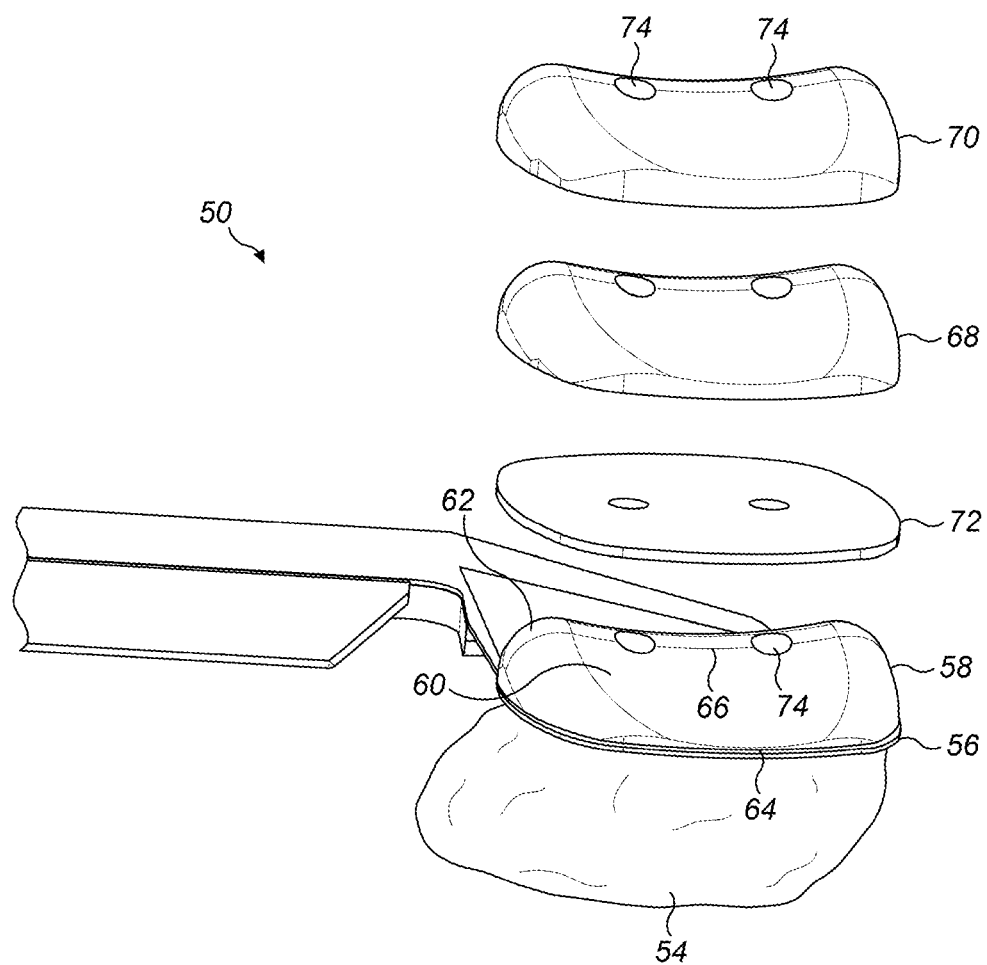
FIG. 7 is an isometric view of a trial patella component kit with a trial patella component in position in relation to a patella, viewed approximately along the medial-lateral axis.

FIG. 7 shows a trial patella component 50 in contact with a patella 54 which has been resected to create a planar resection surface which faces posteriorly. The resection can be performed using a conventional patella resection guide. The depth of the resection is about 5 mm.

The trial patella component 50 comprises a backing plate 56 and a bearing plate 58. The backing plate is made from stainless steel and has a thickness of 1 mm. The bearing plate is formed from glass fibre reinforced nylon and has a planar surface for contacting the backing plate and an opposite bearing surface 60. The bearing surface has a ridge 62 which extends approximately in line with the patient's superior-inferior axis when the trial component is positioned in the patient's joint, extending generally parallel with the medial edge 64 of the plate (and also the lateral edge which is not visible in the drawing). The ridge defines a saddle point 66 at approximately its midpoint. The shape of the bearing surface of the bearing plate shown in FIG. 7 is similar to the shape of the bearing surface of a native patella and is referred to as an anatomic bearing surface.

The backing plate has pins on the surface which faces towards the patella, and which can penetrate the surface of the patella to fix the trial patella component to the patella by preventing it from sliding on the patella. The pins are not visible in the drawing. The backing plate also incorporates force sensors.

The patella kit shown in FIG. 7 includes alternative bearing plates 68, 70, which differ from one another and from the bearing plate which is positioned on the backing plate in terms of their thickness, the difference in thickness between each plate being 1 mm. Each of the bearing plates in the kit shown in FIG. 7 has an anatomic bearing surface.

The kit also includes a shim 72 which can be positioned between the backing plate and a selected one of the bearing plates. The shim is formed from glass reinforced nylon, and is 3D printed. The shim has a thickness of 1 mm.

Each of the bearing plates and the shim has a pair of spaced apart bores 74 extending through it for receiving locating pins which extend from the backing plate. The pins are a sliding fit in the bores in the selected bearing plate, and the shim if used, and serve to locate the selected bearing plate and shim on the backing plate.

Figure 8:
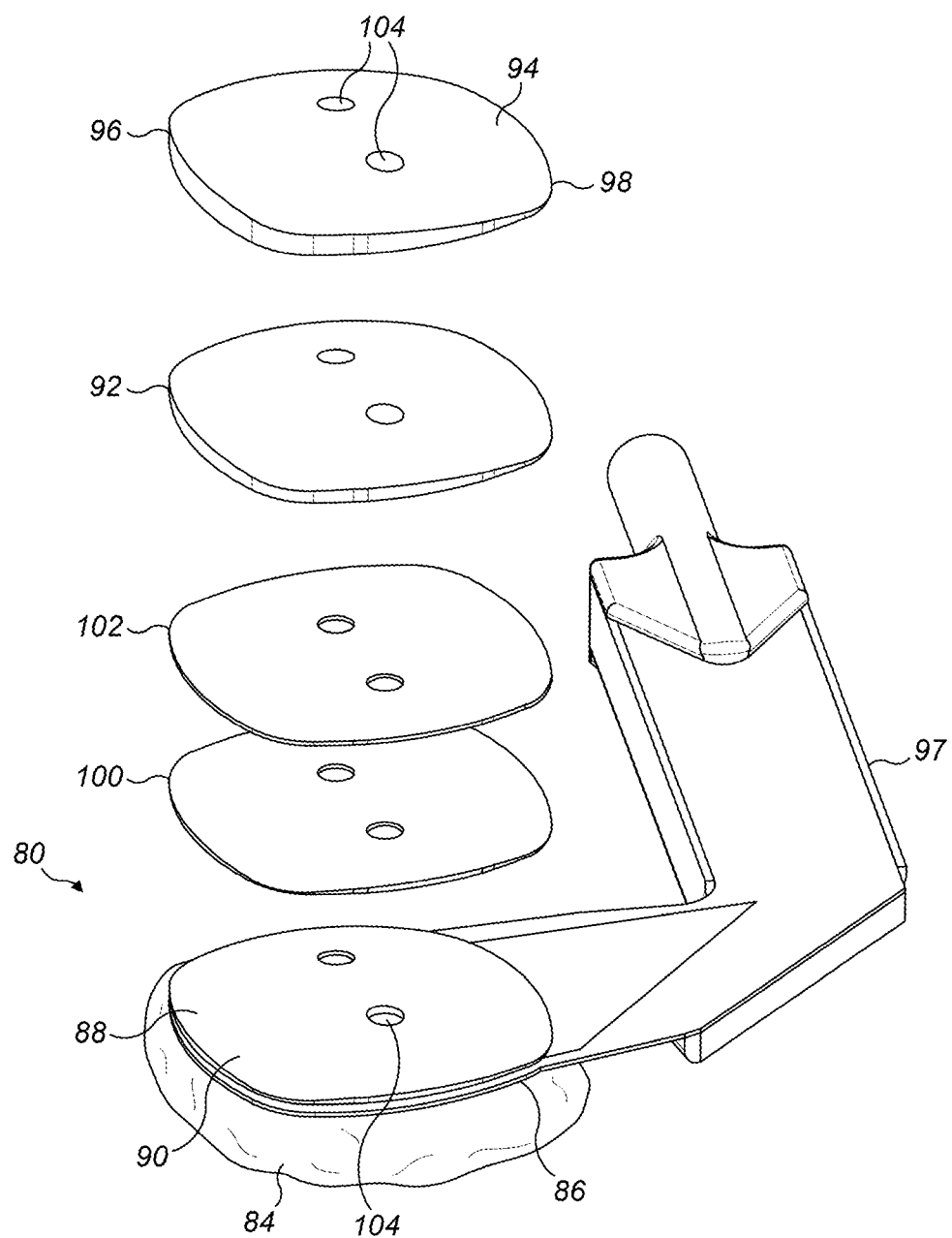
FIG. 8 is an isometric view of another trial patella component kit viewed approximately along the superior-inferior axis.

FIG. 8 shows a trial patella component 80 in contact with a patella 84 which has been resected to create a planar resection surface which faces posteriorly. The resection can be performed using a conventional patella resection guide which can be set to an appropriate resection depth.

The trial patella component 80 comprises a backing plate 86 and a bearing plate 88. The backing plate and the bearing plate are formed from the same materials as the corresponding components in FIG. 7. The bearing plate has a planar surface for contacting the backing plate and an opposite bearing surface 90. The thickness of the bearing plate is greatest at a point that is spaced from all of its edges (medial, lateral, superior, inferior), for example approximately central point. The shape of such a bearing surface is referred to as a domed bearing surface.

The patella kit shown in FIG. 8 includes alternative bearing plates 92, 94, which differ from one another and from the bearing plate which is positioned on the backing plate in terms of difference in thickness in each of the plates between the medial and lateral edges. It can be seen in the drawing that the thickness of the bearing plates 92, 94 is greater at the edge 96 which is remote from the handle 97 than at the edge 98 which is adjacent to the handle. Each of the bearing plates 88, 92, 94 has a thickness of 0.1 mm at the thinnest edge and a thickness at the opposite edge of 1 mm, 2 mm and 3 mm respectively. The bearing plates can be rotated so that the thicker edge can be positioned medial or lateral.

The kit also includes first and second shims 100, 102 which can be positioned between the backing plate and a selected one of the bearing plates. The shims differ from one another in terms of their thicknesses. In a particular embodiment, each of the shims has a constant thickness across its area, the thicknesses being 1 mm, 2 mm and 3 mm respectively. Alternatively, the thickness of a shim might be greater at one edge compared with an opposite edge so that its thickness is tapered. Such a shim can be described as wedge-shaped. In the embodiment of FIG. 8, the shims have thicknesses at the thickest edge of 1 mm, 2 mm and 3 mm respectively. The shims are formed from glass reinforced nylon.

Each of the bearing plates and the shim has a pair of spaced apart bores 104 extending through it for receiving locating pins which extend from the backing plate. The pins are a sliding fit in the bores in the selected bearing plate, and the shim if used, and serve to locate the selected bearing plate and shim on the backing plate.

Figure 9:
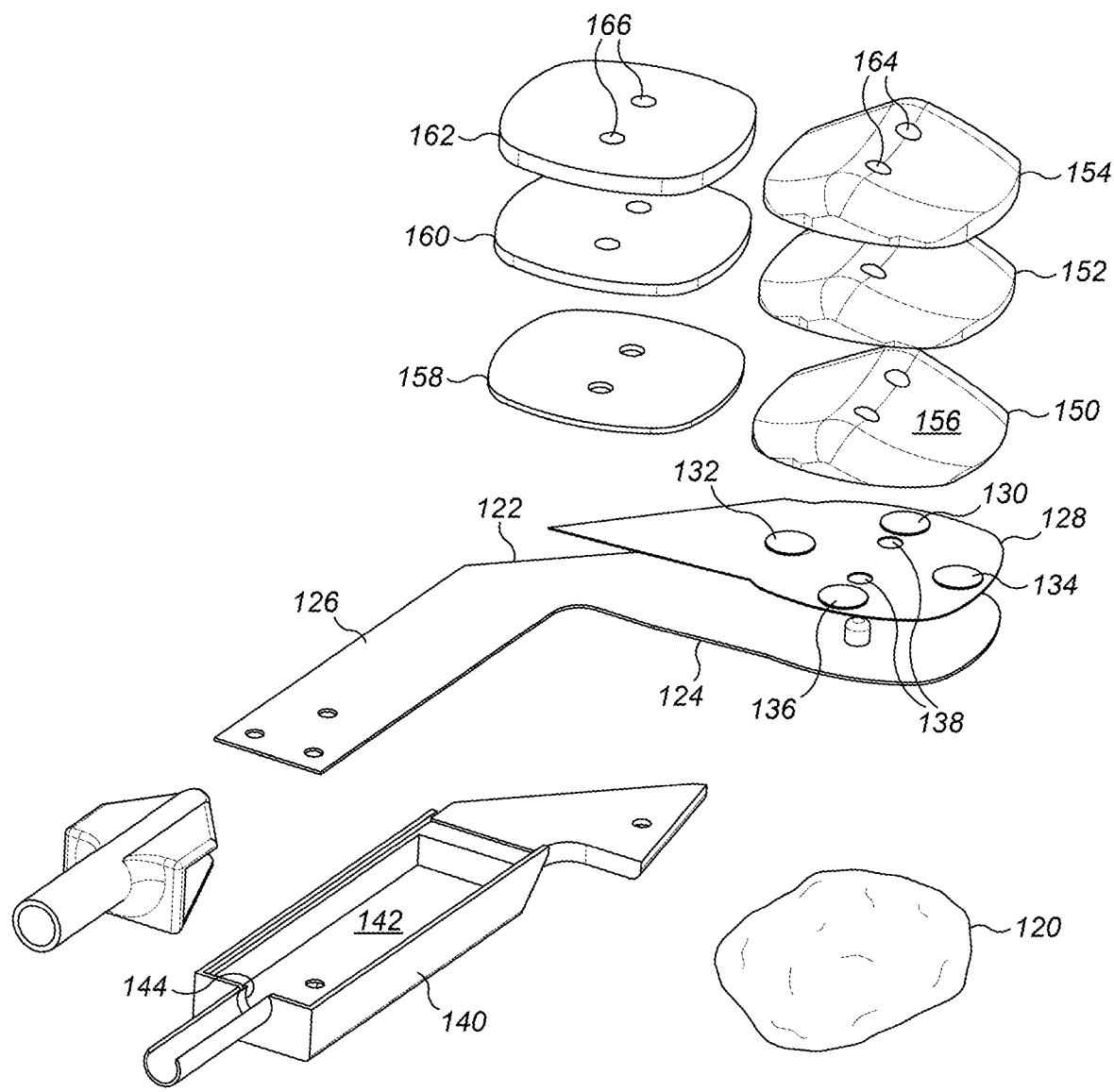
FIG. 9 is an isometric exploded view of a trial patella component kit, similar to that shown in FIG. 7.

FIG. 9 shows a trial patella component positioned in relation to the posterior face of a patella 120. The trial patella component has a backing plate 122. The backing plate has a sensor lobe 124 which can be positioned on a resected surface of the patella and a handle lobe 126. The backing plate is formed from a rigid polymeric material such as a polyamide or a polycarbonate or a polyester, and has a thickness of 0.5 mm. The backing plate has a pair of cylindrical pins extending from its upper face. The pins are spaced apart along the superior-inferior axis. A sensor sheet 128 is positioned on the sensor lobe of the backing plate. The sensor sheet is a FlexiForce HT201 sensor, available from Tekscan Inc. and having a thickness of 0.3 mm, but any conventional sensor could be used. The sensor sheet carries superior, medial, lateral and inferior load sensors 130, 132, 134, 136. The sensor sheet has embedded in it conductors for supplying electrical power to the load sensors and conductors for signals which are generated by the load sensors. The sensor sheet has a pair of holes 138 formed in it in which the pins on the backing plate are a close fit to locate the sensor sheet on the backing plate.

The trial patella component includes a handle 140 which is fastened to the handle lobe 126 of the backing plate. The handle is formed from glass reinforced nylon and includes a chamber 142 having a port 144 for a cable. The chamber can contain connectors between conductors in a cable and the conductors in the sensor sheet. The handle can be gripped by a user of the component. The handle lobe might be truncated or omitted when it is desirable to make the component more compact. A handle might extend transversely without a limb which extends superiorly or inferiorly.

The trial patella component kit includes three bearing plates 150, 152, 154. The bearing face 156 of each of the bearing plates is an anatomic bearing surface, similar to that described above with reference to FIG. 7, and the bearing plates are formed from the same materials as the bearing plates of FIG. 7.

The kit also includes three shims 158, 160, 162. The shims that are shown in FIG. 9 have a constant thickness. Alternatively, one or more of the shims might be thicker at one edge than at its opposite edge so that it is wedge-shaped. The shims are formed from the same materials as the shims of FIG. 8.

Each of the bearing plates has a pair of holes 164 formed in it in which the pins on the backing plate are a close fit to locate a selected one of the bearing plates on the backing plate. Each of the shims has a pair of holes 166 formed in it in which the pins on the backing plate are a close fit. One or more shims can be located on the backing plate, between it and a selected one of the bearing plates.

Figure 10:
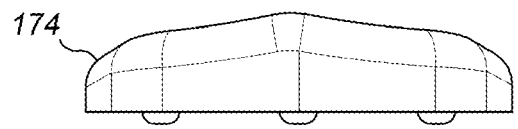
FIGS. 10 and 11 shows elevation views along the superior to inferior axis of sets of bearing plate components which can be used in a trial patella component.
Figure 10:
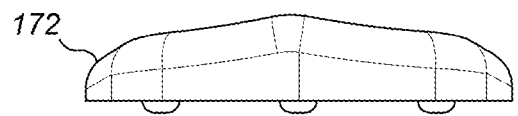
Figure 10:
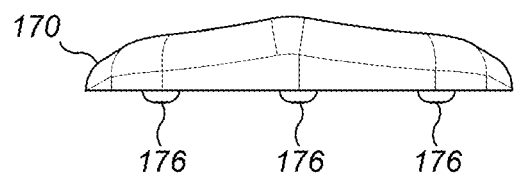

FIG. 10 is a view of the superiorly facing edges of three bearing plates 170, 172, 174. Each of the bearing plates has an anatomic bearing surface. The bearing plates differ from one another in their thicknesses. The difference in thickness between the pairs of plates whose thicknesses are closest is 1 mm. Specifically, the thickness of each bearing plate (excluding the anatomic bearing surface) is 1 mm, 2 mm, and 3 mm.

Each of the bearing plates has pads 176 on its lower surface (opposite to its bearing surface). The positions of the pads correspond to the positions of the load sensors 130, 132, 134, 136 on the sensor sheet 128 so that the pads on a selected one of the bearing plates contact the load sensors when the plate is positioned on the sensor sheet.

Figure 11:
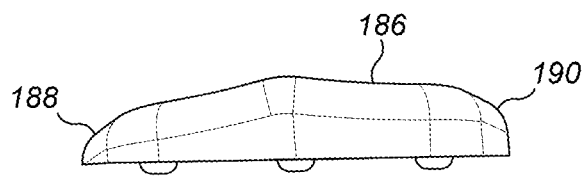
Figure 11:
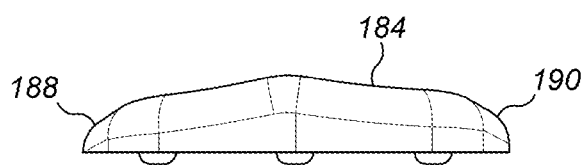
Figure 11:
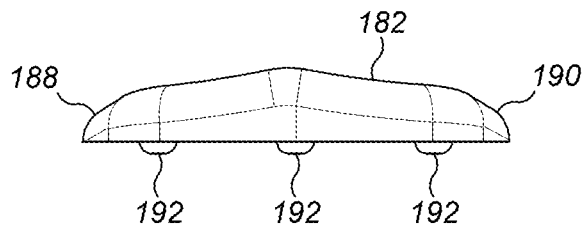

FIG. 11 shows bearing plates 182, 184, 186 also viewed along the superior-inferior axis. Each of the bearing plates has a medial edge 188 and a lateral edge 190. The three bearing plates shown in FIG. 11 have the same thickness at their medial edges. The thicknesses of the three bearing plates shown in FIG. 11 differ at their lateral edges, the difference in thickness being 0.5 mm between each plate. The bearing plates have pads 192 on their lower surfaces.

Figure 12:
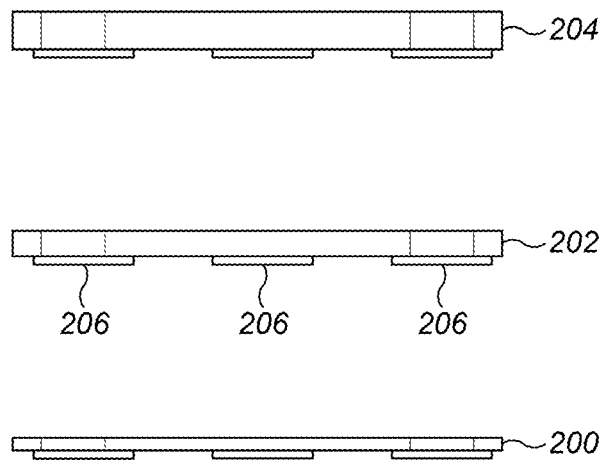
FIG. 12 shows elevation views along the superior to inferior axis of a set of shims which can be used with bearing plate components such as those shown in FIGS. 10 and 11 in a trial patella component.

FIG. 12 is a view of the superiorly facing edges of three shims 200, 202, 204. The shims differ from one another in their thicknesses. The difference in thickness between the pairs of shims whose thicknesses are closest is 1 mm. Specifically, the first shim 200 has a thickness of 1 mm, the second shim 202 has a thickness of 2 mm and the third shim 204 has a thickness of 3 mm. Each of the shims that is shown in FIG. 12 has a constant thickness across its principal surface. Alternatively, one or more of the shims might be thicker at one edge than at its opposite edge so that it is wedge-shaped.

Each of the shims has pads 206 on one of its principal surfaces. The positions of the pads correspond to the positions of the load sensors 130, 132, 134, 136 on the sensor sheet 128 so that the pads on a selected one of the shims contact the load sensors when the shim is positioned on the sensor sheet.

Figure 13:
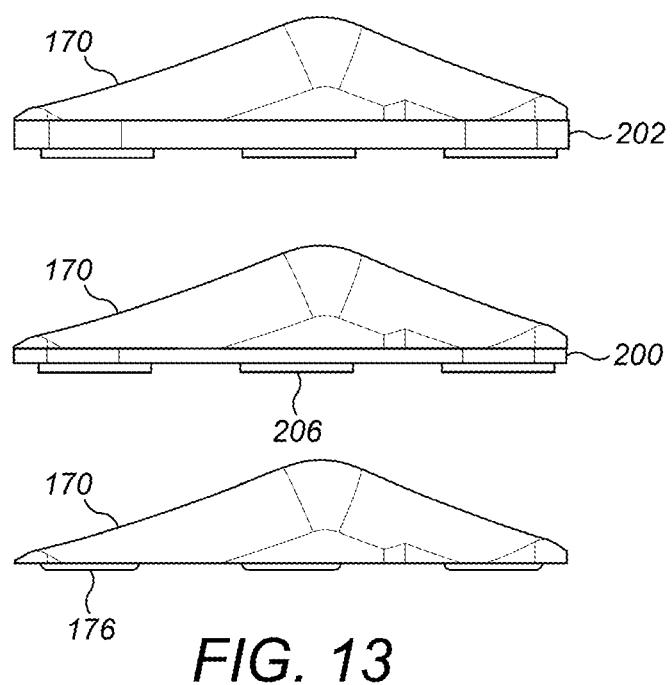
FIG. 13 shows elevation views along the superior to inferior axis of a set of shim and bearing plate component combinations.

FIG. 13 is a view of the superiorly facing edges of three combinations of a backing plate and shim. Each of the combinations uses the thinnest 170 of the bearing plates shown in FIG. 10. The bearing plate is shown with no shim, and with the thinner two 200, 202 of the three shims shown in FIG. 12, respectively.

Figure 14:
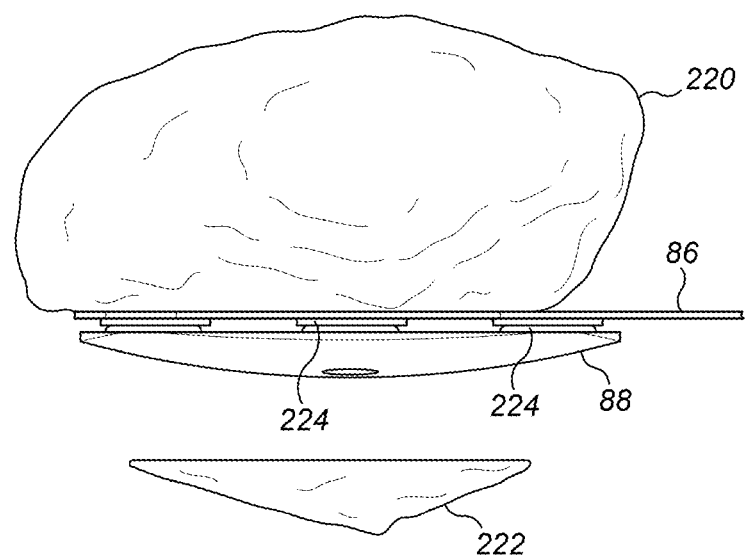
FIG. 14 is an elevation view along the superior to inferior axis of a patella after an initial resection step and with an initial bearing plate in place.

FIG. 14 shows a patella 220 which has been resected to remove its posterior bearing surface. The resected bone material 222 is shown in FIG. 14.

A trial patella component similar to the one shown in FIG. 8 is positioned with the backing plate 86 in contact with the resected patella and a domed bearing plate 88 positioned with the pins on the backing plate received in the bores on the bearing plate. A sensor sheet is located on the backing plate. The bearing plate has pads 224 on the surface which faces towards the backing plate. The bearing plate is positioned so that the pads are in contact with the load sensors on the sensor sheet.

The thickness of the trial patella component that is fitted to the patella immediately after the initial resection corresponds to the depth of the resection. Flexion of the knee with the trial patella component acting against the patient's native femur enables data to be obtained from the load sensors for loads applied to the patella which approximate to the loads that are likely to be experienced in the patient's native patella.

Figure 15:
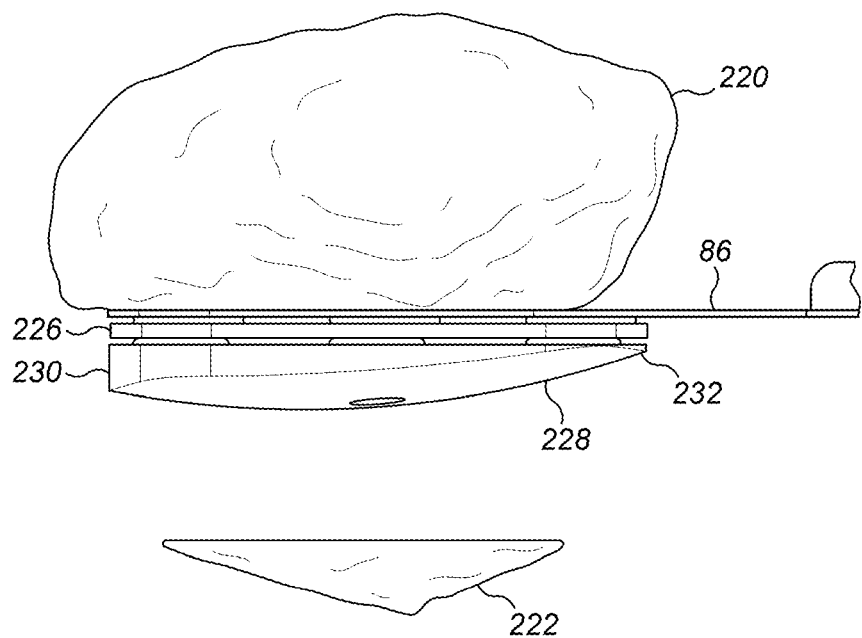
FIG. 15 is another elevation view along the superior to inferior axis of the patella as shown in FIG. 14, with a different bearing plate assembly in place.

FIG. 15 shows the patella 220 and the trial patella component with the backing plate 86 in contact with the patella. The trial patella in the configuration shown in FIG. 16 has a shim 226 and a bearing plate 228 whose thickness at its lateral edge 230 is 3 mm and the thickness at its medial edge 232 is 1 mm.

The kit provided by the invention can be used in a surgical procedure as follows:

A first step in the procedure which involves the kit of the invention is a conservative resection of the patella. The trial patella component is then fitted to the resected patella with the backing plate pressed against the surface of the patella which is exposed by the resection and pins on the backing plate penetrating into the resected patella so as to fix the backing plate to the patella, by preventing it from sliding on the patella.

The thickness of the trial patella component, made up of the bearing plate and the backing plate, corresponds to the thickness of bone that is removed in the conservative resection.

The joint is then flexed with the bearing surface provided by the bearing plate of the trial patella component acting against the bearing surface of the patient's natural femur. The load to which the patella is subjected can be measured throughout the range of motion of the joint using the trial patella component.

The surgical procedure then involves locating the planes for resection of the patient's femur and tibia using conventional instrumentation, and fitting trial femoral and tibial components to the resected bones.

The joint is flexed with the trial femoral and tibial components in place, and with the bearing surface provided by the bearing plate of the trial patella component acting against the bearing surface provided by the trial femoral component. The load to which the patella is subjected can be measured throughout the range of motion of the joint using the trial patella component. The load to which the patella is subjected can be increased by substitution of the bearing plate component of the trial patella component by a bearing plate having a greater thickness. The load to which the patella is subjected can be reduced by substitution of the bearing plate component of the trial patella component by a bearing plate having a smaller thickness or having different thickness different between opposite edges. The substitution of the bearing plate component has the aim to achieve a desirable tension in the patient's quadriceps muscle throughout the range of motion of the joint, frequently as similar as possible to that in the quadriceps muscle at the start of the procedure. Features which it can be desirable to match include the absolute load sensed by each sensor, the difference in loads between pairs of sensors (for example between medial and lateral sensors), and the flexion angles at which peak load is sensed by one or more of the sensors. Bearing plates having thicknesses from 2 mm to 7 mm, and with differences in thickness between opposite edges of 1 mm or 2 mm, might be included in the kit for this purpose.

The total thickness of the trial patella component, with the selected bearing plate, allows the surgeon to determine the amount of patella tissue that should be removed in a second resection which creates the resection surface which a patella implant component can be fitted to, with the intention of ensuring that the total effective thickness of the patella with the trial patella component in place is the same as the total effective thickness of the patella with the patella implant component in place, taking into account the greater thickness of the patella implant component compared with the trial patella component with its selected bearing plate.

FIGS. 16 to 21 show the variation in load sensed by lateral, superior and medial sensors in a trial patella component of the kind described above with reference to FIG. 8. The data have been obtained using a sawbones model, and using components from a knee replacement system as sold by DePuy International Limited under the trade mark Attune.

Figure 16:
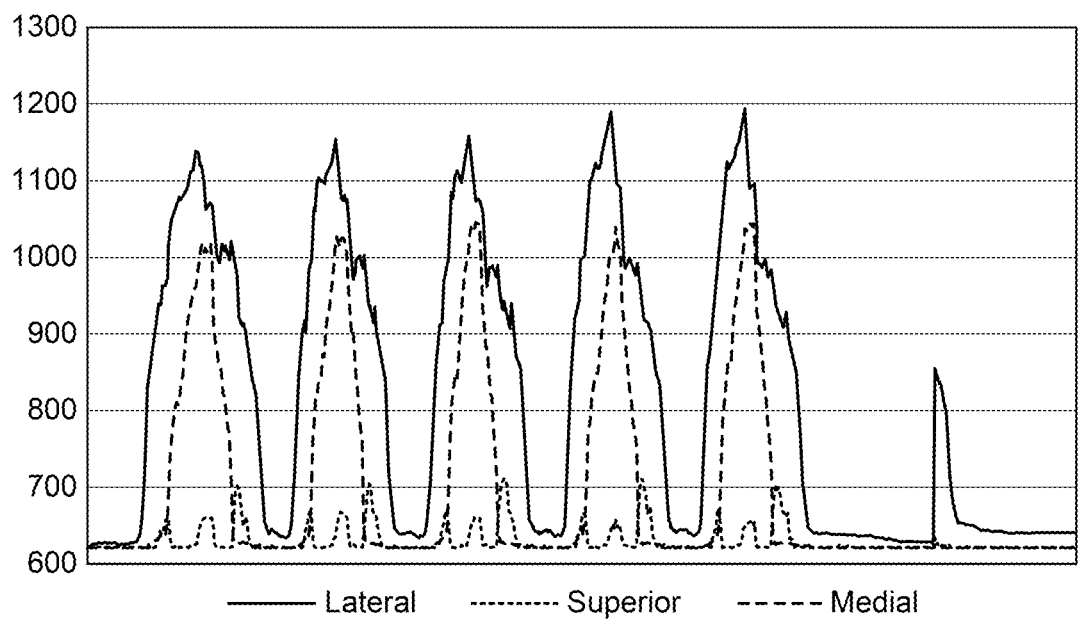
FIGS. 16 to 21 are graphs which show the variation in load that is sensed by lateral, superior and medial load sensors on a trial patella component during flexion, in which the y-axis units reflect the electrical output from the load sensors which is an indication of sensed load.

FIG. 16 shows the variation in load using a trial patella component after performing a conservative resection on the patella, as described above with reference to FIG. 14. The trial patella component articulated against the bearing surface provided by the femur component of the sawbones model.

The femur and tibia were then prepared for receiving femoral and tibial trials respectively by performing (a) a 9 mm distal femoral cut with a 5 degree varus valgus adjustment, (b) a 9 mm tibial resection with a 5 degree anterior slope, and (c) posterior femoral cuts using a size 5 cutting block, set in the neutral position.

Figure 17:
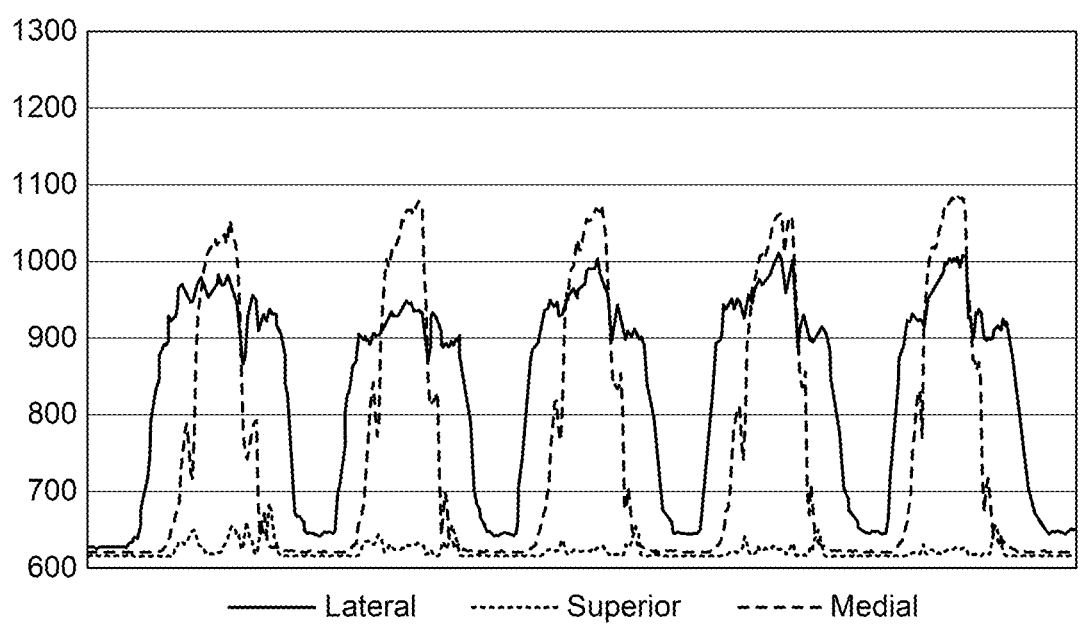
Figure 18:
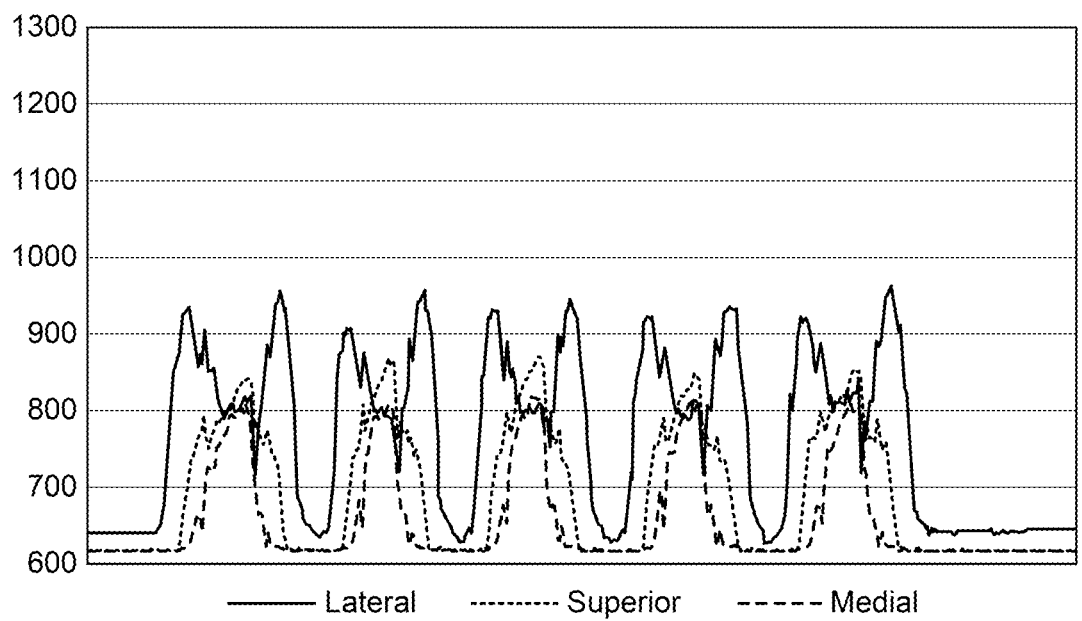

The model knee was then flexed with the trial patella component in place, fitted with constant thickness bearing plates, of the type shown in FIG. 10. The variation in load during flexion is shown in FIGS. 17 (5 mm bearing plate) and 18 (7 mm bearing plate).

Figure 19:
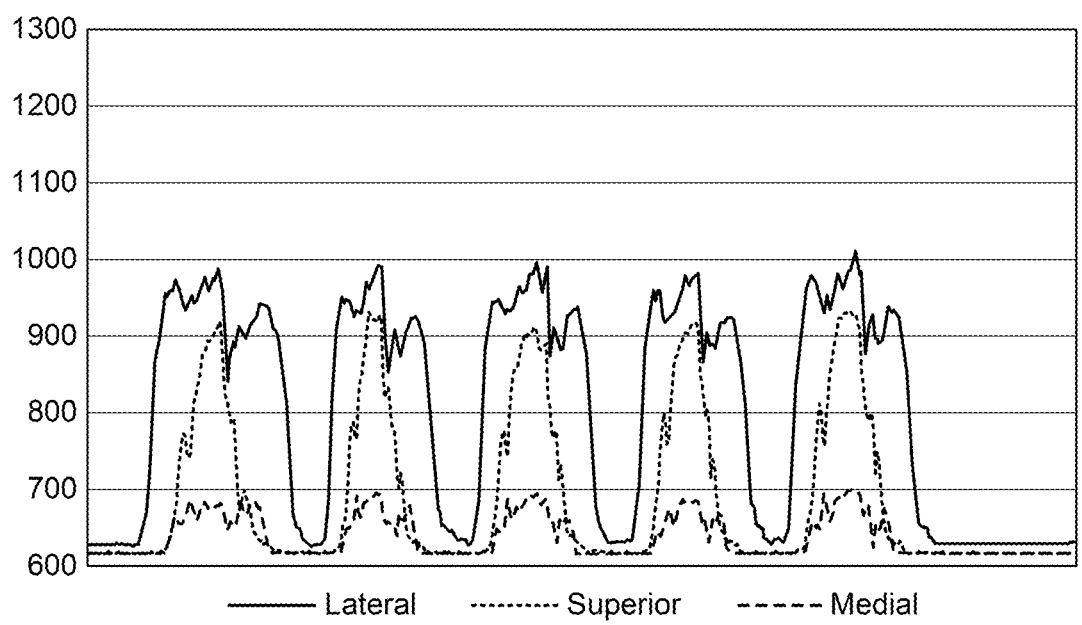
Figure 20:
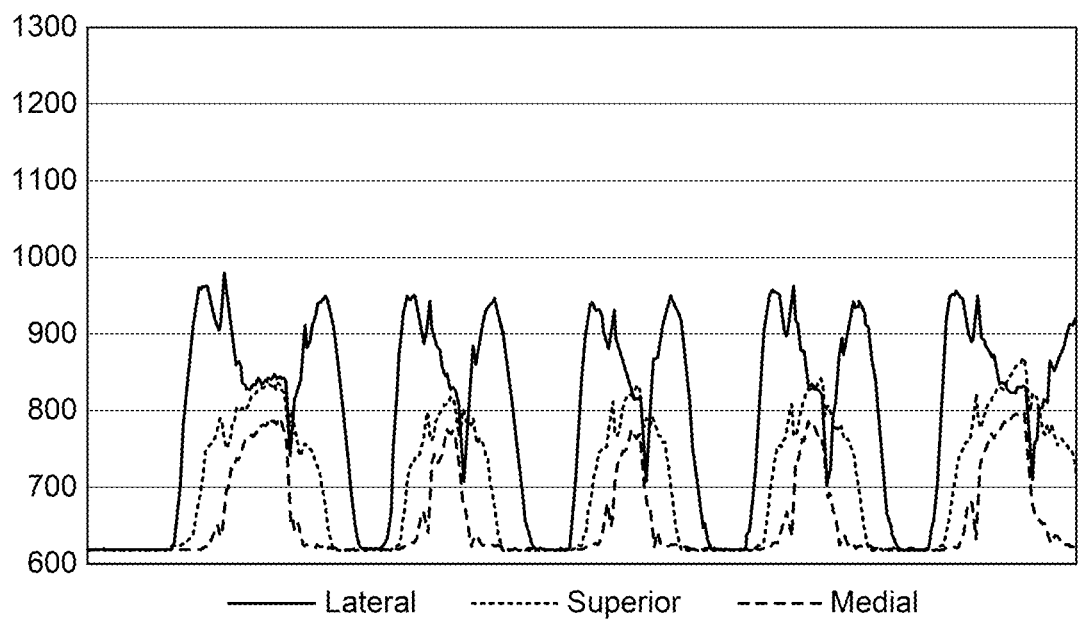

The model knee was then flexed with bearing plates whose thicknesses differ between the medial and lateral edges. The bearing plates were of the type shown in FIG. 11, with shims as shown in FIG. 12. The variation in load during flexion is shown in FIGS. 19 (bearing plate thickness: 5 mm medial; 6 mm lateral), 20 (bearing plate thickness: 7 mm medial; 8 mm lateral) and 21 (bearing plate thickness: 6 mm medial; 7 mm lateral).

Figure 21:
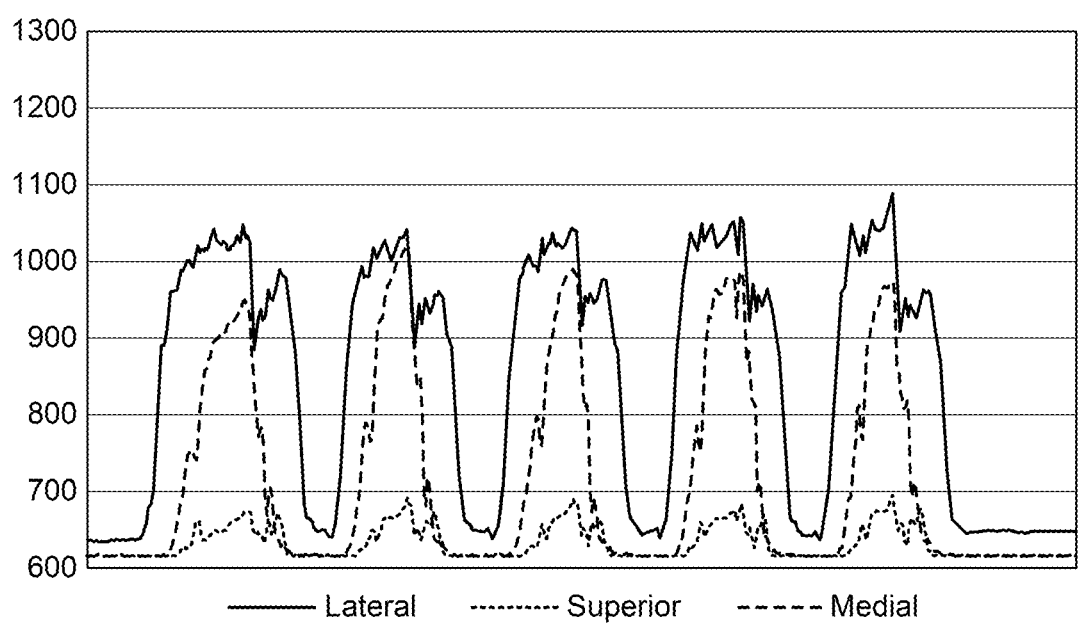

It can be seen that there are similarities between the load variation graphs in FIGS. 16 and 21 in the maximum loads sensed by the three sensors and the relationship between the flexion angles at which those maximum loads are sensed.

Figure 22:
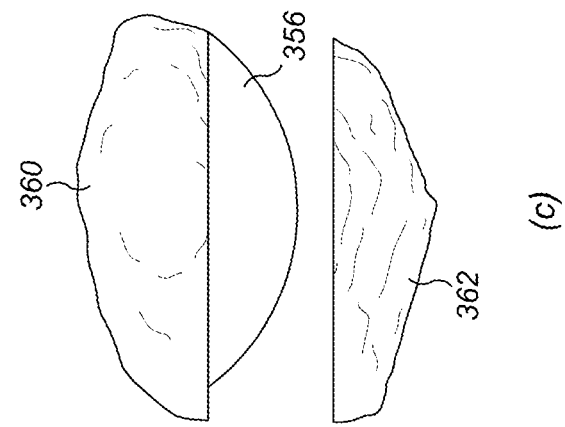
Figure 22:
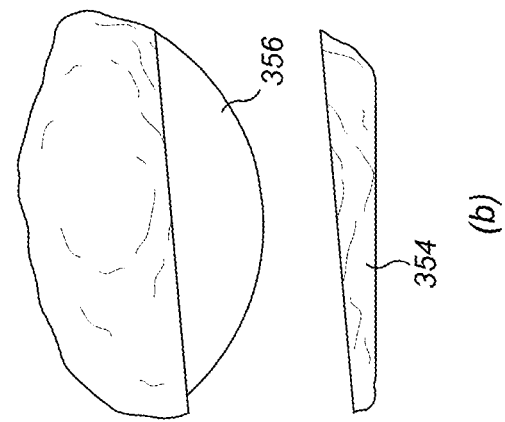
Figure 22:
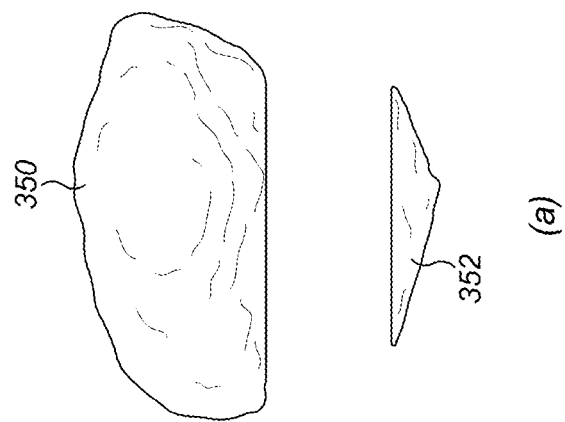

The nature of the two step resection that is intended when using the kit of the invention can be understood with reference to FIG. 22. FIG. 22(a) shows a patella 350 after the initial shallow resection step to remove a portion 352 of the patella having a depth of about 4 to 5 mm. FIG. 22(b) shows the patella after the second resection step to remove a further portion 354 of the patella and fitting of an implant component 356 to the patella. In contrast, FIG. 22(c) shows the result of a conventional procedure in which a single resection step is performed on a patella 360 to remove a portion of the patella 362 prior to fitting the implant component 356. The depth of the portion 362 of the patella that is removed using the conventional procedure is more than the sum of the depths of the portions 352, 354 of the patella that are removed when the kit of the present invention is used. Furthermore the present invention enables the orientation of the final resection plane of the patella to be selected as can be seen from the shape of the further resection portion 354 shown in FIG. 22(b).

Figure 23:
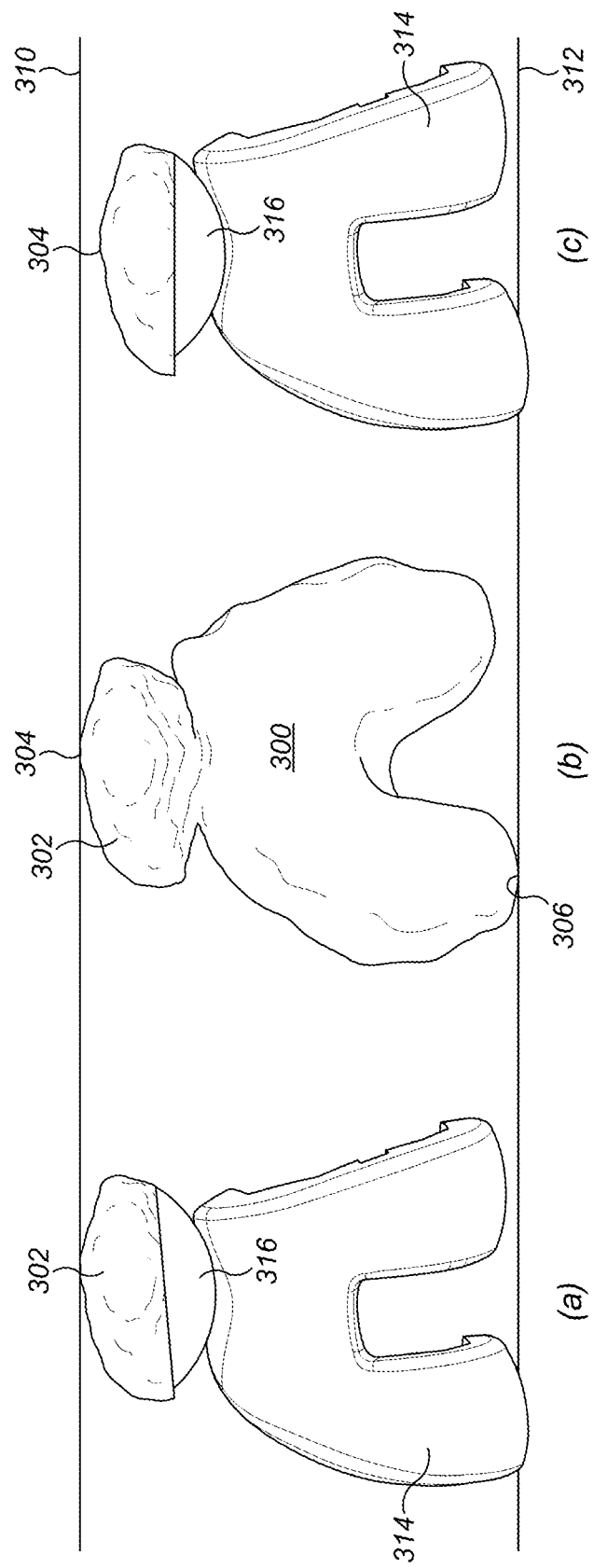

FIG. 23 depicts schematically views of three femur-patella combinations, showing the distal face of the femur 300 and the patella 302 in contact with the femur in the position that it has when the knee is extended.

FIG. 23(b) shows a natural knee in which the anterior face 304 of the patella 302 defines an anterior guide line 310 and the posterior femoral condyles 306 define a posterior guide line 312.

FIG. 23(c) shows a knee in which a femoral implant component 314 has been fitted to the femur 300 and a patella implant component 316 has been fitted to the patella 302. It can be seen that the bearing surface provided by the femoral implant component varies from the bearing surface provided in the natural knee in that the posterior condyle 306 is located posteriorly of the posterior guide line 312. This can result from the steps taken to position the tibial and femoral components of the prosthesis and is a normal occurrence.

Following conventional knee replacement surgical procedures, the thickness of the patella implant component will be chosen so that it matches the thickness of the portion of the patella that is resected. The consequence of this, as shown in FIG. 3(c) is that the anterior face 304 of the patella 302 is located posteriorly of the anterior guide line 310, and the tension in soft tissue connected to the patella will be less than in the natural knee.

FIG. 23(a) shows that a smaller final resection of the patella, as described above with reference to FIGS. 22(a) and (b), can restore the position of the patella relative to the anterior guide line and therefore restore the tension in soft tissue connected to the patella so that it is closer to that in the natural knee. As discussed herein, the invention facilitates identification of the appropriate plane for resection of the patella to achieve this result. This can provide better balance in the patient's quadriceps mechanism which can improve the long term outcome of the knee replacement procedure.

What is claimed is:

1. A method of knee replacement surgery which comprises:
   a. performing a first resection on a patella of a patient, thereby forming a resected patella;
   b. fitting to the resected patella a trial patella component comprising:
      i. a backing plate having at least one sensor which can generate a signal corresponding to the compressive load applied to the backing plate, and
      ii. a first bearing plate which can be fitted to the backing plate and which, when fitted to the backing plate, provides a bearing surface for articulation with a bearing surface on a femur of the patient,
   c. articulating a knee joint to which the trial patella component is fitted to obtain information from the at least one sensor concerning tension in soft tissue which is connected to the patella as the patella articulates against an existing femoral bearing surface of the patient,
   d. fitting a femoral trial component to the femur of the patient,
   e. articulating the knee joint to obtain information from the sensor concerning tension in soft tissue which is connected to the patella as the patella articulates against a surface provided by the femoral trial component,
   f. identifying a location of a second resection of the patella to receive a patella implant component having a thickness greater than a thickness of the trial patella component, to provide a desired tension in soft tissue which is connected to the patella as the patella articulates against a femoral implant component in a completed replacement joint,
   g. performing a second resection on the patella, and
   h. fitting the patella implant component to the patella.

2. A method as claimed in claim 1, in which the thickness of the patella implant component is greater than the thickness of the trial patella component when the first bearing plate is fitted to the backing plate, the difference between the said thicknesses being at least about 1 mm.

3. A method as claimed in claim 2, in which the difference between the thickness of the patella implant component and the thickness of the trial patella component which is provided by the backing plate and the first bearing plate is at least about 3 mm.

4. A method as claimed in claim 1, which includes fitting a differential thickness bearing plate to the backing plate instead of the first bearing plate, in which the differential thickness bearing plate, when fitted to the backing plate, provides a bearing surface for articulation with a bearing surface on the femur, and in which a thickness of the differential thickness bearing plate is less than the thickness of the first bearing plate.

5. A method as claimed in claim 1, which includes fitting a differential inclination bearing plate to the backing plate instead of the first bearing plate, in which the differential inclination bearing plate, when fitted to the backing plate, provides a bearing surface for articulation against a bearing surface on the femur, and in which the difference in thickness between first and second opposite edges of the first bearing plate is different from the difference in thickness between corresponding first and second edges of the differential inclination bearing plate.

6. A method as claimed in claim 1, which includes fitting a first shim between the backing plate and the first bearing plate.

7. A method as claimed in claim 6, which includes fitting a second shim between the backing plate and the first bearing plate instead of or in addition to the first shim.

8. A method as claimed in claim 7, in which a thickness of the second shim is different from a thickness of the first shim.

9. A method as claimed in claim 7, in which a difference in thickness between medial and lateral edges of the first shim is different from a difference in thickness between medial and lateral edges of the second shim.

10. A method as claimed in claim 1, in which the thickness of the trial patella component which is provided by the backing plate and the first bearing plate is not more than about 6 mm.

11. A method as claimed in claim 10, in which the thickness of the patella implant component is at least about 7 mm.

12. A method as claimed in claim 1, in which at least one pin on the backing plate is made to penetrate a prepared surface of a patient's patella to locate the backing plate on the patella.

13. A method as claimed in any claim 1, which includes removably fixing the backing plate on the bearing plate.

14. A method as claimed in claim 1, in which the backing plate has at least two sensors which are spaced apart along a superior-inferior axis and/or in which the backing plate has at least two sensors which are spaced apart along a medial-lateral axis.

* * * * *